(12) United States Patent
Dungy

(10) Patent No.: US 10,206,696 B2
(45) Date of Patent: Feb. 19, 2019

(54) DEVICES AND METHODS FOR ESTABLISHING FEMORAL AND TIBIAL RESECTION POSITIONS IN A TOTAL KNEE REPLACEMENT PROCEDURE

(71) Applicant: Danton S. Dungy, Scottsdale, AZ (US)

(72) Inventor: Danton S. Dungy, Scottsdale, AZ (US)

( * ) Notice: Subject to any disclaimer, the term of this patent is extended or adjusted under 35 U.S.C. 154(b) by 802 days.

(21) Appl. No.: 14/593,814

(22) Filed: Jan. 9, 2015

(65) Prior Publication Data

US 2016/0199077 A1 Jul. 14, 2016

(51) Int. Cl.
  *A61B 17/15* (2006.01)
  *A61B 17/02* (2006.01)
  *A61B 17/17* (2006.01)
  *A61B 90/00* (2016.01)

(52) U.S. Cl.
  CPC ........ *A61B 17/1764* (2013.01); *A61B 17/025* (2013.01); *A61B 17/155* (2013.01); *A61B 17/157* (2013.01); *A61B 2017/0268* (2013.01); *A61B 2090/067* (2016.02)

(58) Field of Classification Search
  CPC ................ A61B 17/154; A61B 17/155; A61B 2017/0268
  See application file for complete search history.

(56) References Cited

U.S. PATENT DOCUMENTS

| | | |
|---|---|---|
| 4,501,266 A | 2/1985 | McDaniel |
| 4,566,448 A | 1/1986 | Rohr, Jr. |
| 5,597,379 A | 1/1997 | Haines et al. |
| 5,669,914 A * | 9/1997 | Eckhoff ............... A61B 17/157 606/102 |
| 5,735,904 A | 4/1998 | Pappas |
| 6,258,096 B1 | 7/2001 | Seki |
| 7,641,663 B2 | 1/2010 | Hodorek |
| 7,704,253 B2 | 4/2010 | Bastian et al. |
| 7,727,238 B2 * | 6/2010 | Seo ...................... A61B 17/155 606/102 |
| 8,162,951 B2 * | 4/2012 | Kaufman ............. A61B 17/025 33/797 |
| 8,257,360 B2 | 9/2012 | Richard et al. |
| 8,286,362 B2 * | 10/2012 | Petersheim .............. G01B 5/14 33/542 |
| 8,529,573 B2 | 9/2013 | McAllister et al. |

* cited by examiner

*Primary Examiner* — Nicholas Woodall
(74) *Attorney, Agent, or Firm* — Snell & Wilmer L.L.P.

(57) ABSTRACT

Devices, kits, and methods that may be used to establish a distal femoral resection position or a proximal tibial resection position and a prosthetic gap in a total knee arthroplasty procedure are provided. Devices for establishing a distal femoral resection position or a proximal tibial resection position may comprise a support that attaches to and references a proximal resected tibia or distal resected femur and supports and establishes the position of a resection guide. A kit may comprise a device for establishing a distal femoral resection position or proximal tibial resection position and additional components that complement the device or facilitate application of the device during a total knee arthroplasty procedure. Methods for establishing a distal femoral resection position or a proximal tibial resection position are also provided.

14 Claims, 11 Drawing Sheets

400

DEVICES AND METHODS FOR ESTABLISHING FEMORAL AND TIBIAL RESECTION POSITIONS IN A TOTAL KNEE REPLACEMENT PROCEDURE

FIELD

The present disclosure relates generally to devices, methods, and kits for performing a total knee replacement, and more particularly to devices, methods, and kits for establishing a position of a distal femoral resection or a proximal tibial resection with reference to an opposing resected surface to produce a desired prosthetic gap.

BACKGROUND

A variety of approaches are available for surgical preparation of a knee to receive a prosthetic joint in a total knee replacement procedure (also referred to as a total knee arthroplasty). Commonly used approaches rely on insertion of a rod into the distal femur (i.e., intramedullary approaches) to establish the alignment of the femoral axis and determine the orientation of the cut for resection of the distal femur. In addition, various surgical approaches also commonly rely on performing soft tissue releases, or cutting the medial and lateral collateral ligaments, to balance ligamentous tension in the joint in the course of surgically preparing a knee to receive a prosthetic joint.

The approaches relying on the steps described above can be complex, and the surgical steps themselves are traumatic for the patient. Violation of the femoral medullary canal by insertion of an intramedullary rod destroys femoral medullary tissues and can produce substantial bleeding, increasing risks of complications due to blood loss, requirement for transfusion, embolism, and the like. Furthermore, the intramedullary rod insertion angle may not accurately reflect the true femoral axis (i.e., the mechanical axis), which can lead to imprecisions in subsequent surgical steps and non-optimal prosthetic joint alignment and performance. Likewise, soft tissue releases that are often performed to provide balanced ligamentous tension around the prosthetic gap increase the risk of iatrogenic instability.

Thus, the effects of common surgical approaches to performing a total knee arthroplasty can produce substantial cumulative trauma to the knee and result in long recovery times. Likewise, intramedullary approaches to determining bone resection alignment and performance soft tissue releases to balance the joint are subject to imprecisions that may lead to misalignment of the implanted joint, resulting in post-recovery pain and poor joint function.

Therefore, devices and methods for establishing a distal femoral resection position to provide a prosthetic gap with balanced ligamentous tension, without violating the femoral medullary canal and without the need for soft tissue releases, are desirable. Likewise, devices and methods for establishing a proximal tibial resection relative to a resected distal femur without the need for soft tissue releases are also desirable.

SUMMARY

A device for establishing a distal femoral resection position in a total knee replacement procedure may comprise a tibial support and a femoral resection guide. The tibial support may further comprise a femoral resection guide alignment arm that may be detachably coupled to a femoral resection guide using a coupling component. An alignment arm may be configured to be adjustably coupled to the femoral resection guide to provide a range of relative positions of the tibial support and the femoral resection guide. The tibial support and the femoral resection guide may comprise pin bores for attachment to a tibia and femur. The femoral resection guide may further comprise a guide slot to guide resection of a distal femur. The tibial support and/or the femoral resection guide may be modular and comprise cutouts configured to receive corresponding inserts that may be used to adapt a device to a variety of specific surgical applications.

A kit for establishing a distal femoral resection position in a total knee arthroplasty is also provided. A kit may comprise a device for establishing a distal femoral resection position, including a tibial support, a femoral resection guide, and a coupling component. A tibial support may comprise a tibial support cutout configured to receive a tibial support insert. A kit may comprise a device for establishing a proximal tibial resection position having similar features to a device for establishing a distal femoral resection position. A kit may also comprise one or more joint distraction devices such as a femoral tibial spreader. A kit may also comprise a transverse surface contact plate. A kit may further comprise a tibial support or a femoral support insert. A tibial support insert or a femoral support insert may be comprised of a polymeric material. A kit may comprise an adjustable angle alignment arm that may be attached to a transverse surface contact plate and used to support a tibial or femoral resection guide. A kit may also comprise an angle validation tool.

A method for establishing a distal femoral resection position to provide a prosthetic gap is provided. A method for establishing a distal femoral resection position may comprise attaching a tibial support of a device for establishing a distal femoral resection position to a proximal resected tibia. A method may further comprise distracting a resected proximal tibia from a non-resected distal femur. A method may further comprise adjusting a position of a femoral resection guide relative to a tibial support and securing the femoral resection guide to the tibial support. The method may further comprise attaching the femoral resection guide to an anterior aspect of the distal femur, and may optionally further comprise performing a resection of the distal femur using a guide slot disposed in the femoral resection guide.

A method for establishing a proximal tibial resection position to provide a prosthetic gap is provided. A method for establishing a proximal tibial resection position may comprise applying a transverse surface contact plate to a resected surfaced of a distal femur. A method may further comprise attaching a device for establishing a proximal tibial resection position to the distal femur. A method may comprise distracting the proximal tibia from the resected distal femur. A tibial resection guide may then be attached to the proximal tibia. The proximal-distal position of the tibial resection guide may then be optionally adjusted. Resection may then optionally be performed, optionally followed by verification of the resection angle using an angle validation tool.

BRIEF DESCRIPTION OF THE DRAWINGS

A more complete understanding may be derived by referring to the detailed description and claims when considered in connection with the Figures, wherein like reference numbers refer to similar elements throughout the Figures, and wherein:

DETAILED DESCRIPTION

Figure 1A:
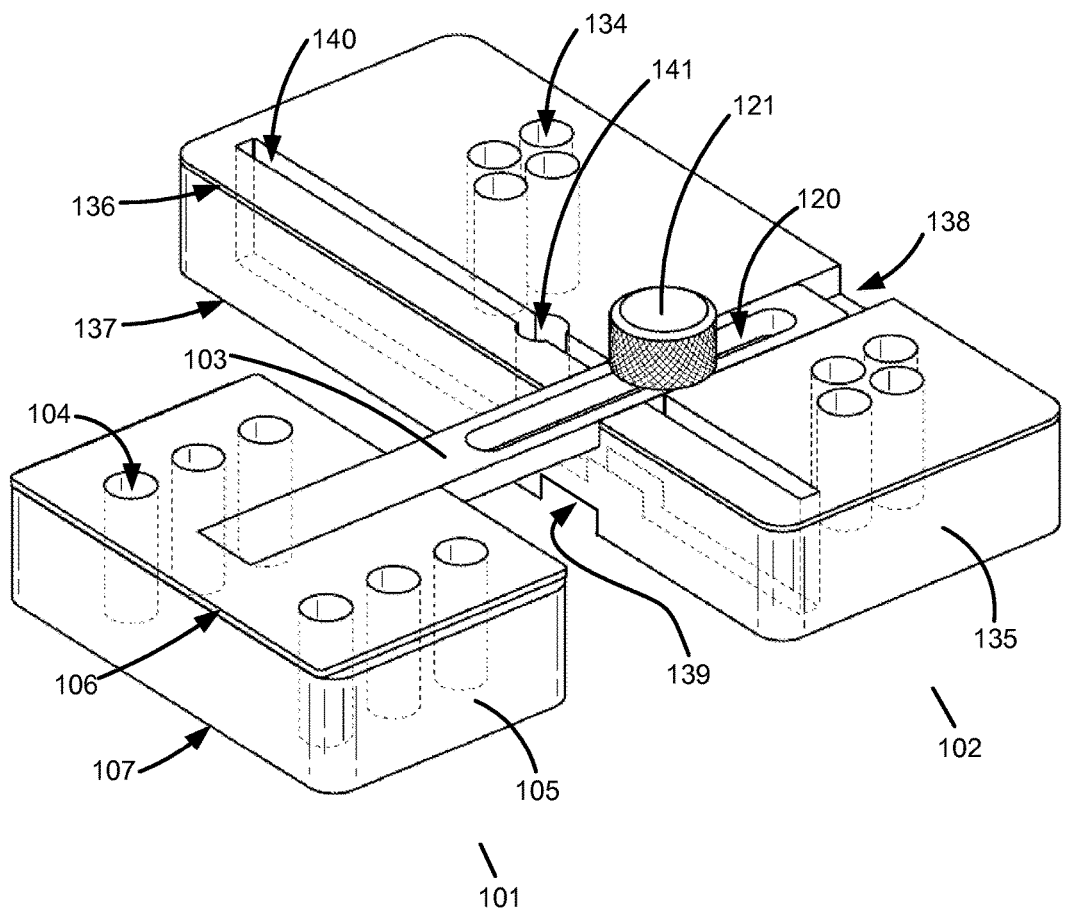
FIG. 1A illustrates a perspective view of a device according to various embodiments of the disclosure.

The detailed description of exemplary embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not of limitation. For example, the steps recited in any of the method or process descriptions may be executed in any order and are not limited to the order presented. Furthermore, any reference to singular includes plural embodiments, and any reference to more than one component may include a singular embodiment.

Various devices, kits, and methods are provided in this disclosure. In the detailed description herein, references to "various embodiments," "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to include such feature, structure, or characteristic in connection with other embodiments whether or not explicitly described. After reading the description, it will be apparent to one skilled in the relevant art(s) how to implement the disclosure in alternative embodiments.

Devices, kits, and methods facilitating establishing a distal femoral resection position or a proximal tibial resection position in a total knee arthroplasty procedure are disclosed according to various embodiments. Although the present disclosure describes devices, kits, and methods in relation to a total knee arthroplasty procedure, a person of skill in the art will appreciate that the configuration of the various devices, device components, and methods described herein may be readily modified or adapted for application in other joints or portions of a patient's body, and such other applications are contemplated within the scope of the present disclosure.

As used herein, the term "prosthetic gap" means the gap between a patient's bones required to accommodate implantation of a prosthetic device, such as an artificial knee. For example, implantation of an artificial knee may require resection of a patient's proximal tibia and distal femur, with removal of a sufficient amount of bone tissue to permit replacement by a prosthetic joint having a particular height in the gap between the resected bones. Likewise, the term "prosthetic gap" also includes the relative alignment of the resected surfaces of the bones between which the gap is established. Finally, the term "prosthetic gap" can be used to refer to an actual prosthetic gap, or a planned prosthetic gap that will have desired features or characteristics following a distal femoral resection step required to achieve the actual prosthetic gap.

In various embodiments, a device for establishing a distal femoral resection position in a total knee arthroplasty procedure comprises an adjustable device that can be removably attached to a patient's tibia and femur. The device can comprise a tibial support and a femoral resection guide. The tibial support of a device may be attached to the patient's proximal tibia after the tibia has been resected. A femoral resection guide alignment arm extends from the tibial support and can be adjustably coupled to the femoral resection guide by a coupling component. When the tibial support is coupled to the femoral resection guide, the device may provide a predetermined alignment between the tibial support and the femoral resection guide. The femoral resection guide can be removably attached to the distal femur after it is coupled to the tibial support. After attachment to the femur, the femoral resection guide can be uncoupled from the tibial support and be used as a guide for resection of the distal femur. Performing a resection of the distal femur using the femoral resection guide may produce a resected surface of the distal femur surface with a predetermined alignment relative to the resected surface of the proximal tibia and a desired prosthetic gap.

In various embodiments, a device for establishing a proximal tibial resection position is also provided. A device for establishing a proximal tibial resection may comprise various features and characteristics similar to those described in detail herein relative to a device for establishing a distal femoral resection. Likewise, a device for establishing a proximal tibial resection may perform various similar functions to those of a device for establishing a distal femoral resection, described in detail below.

Figure 1B:
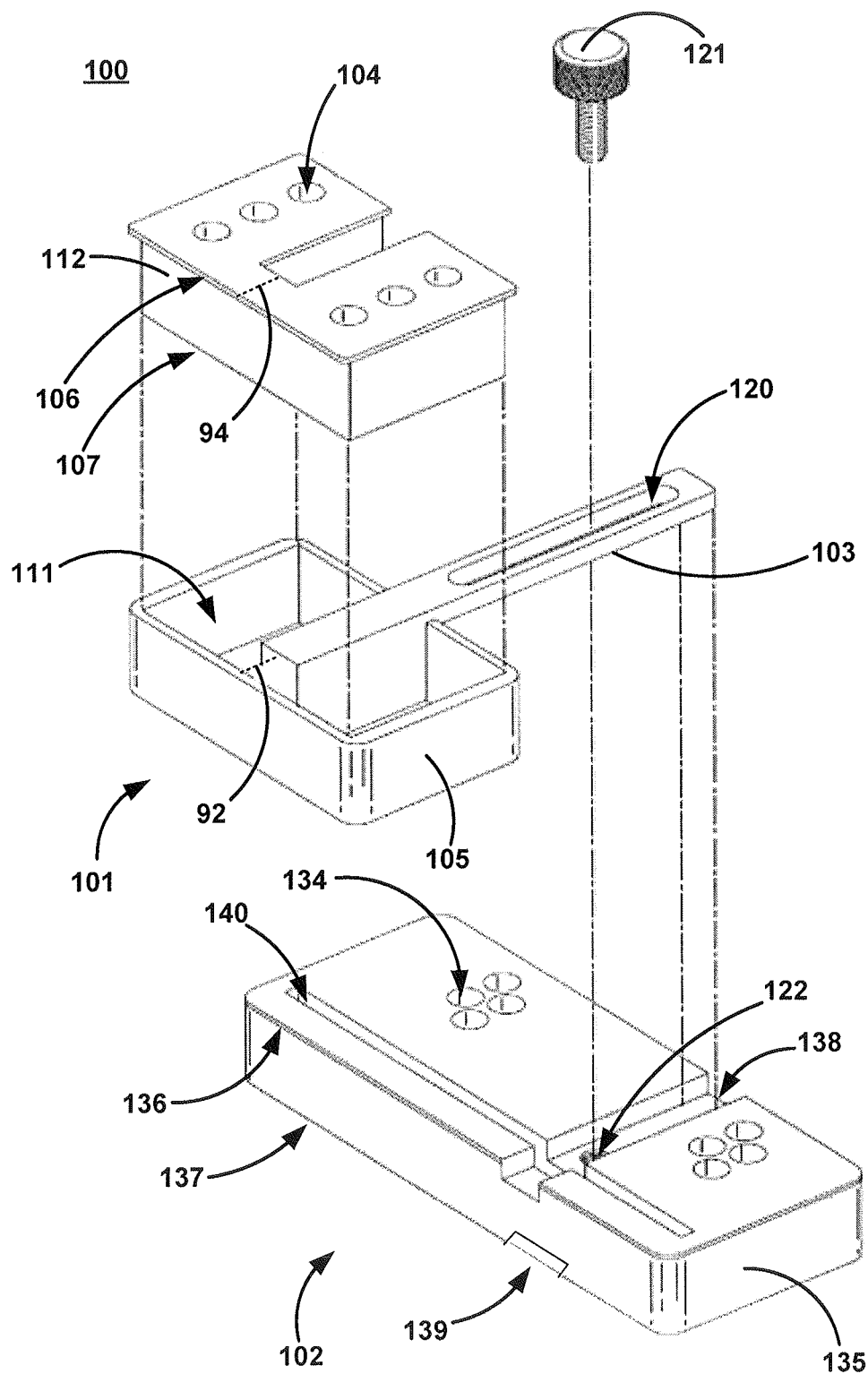
FIG. 1B illustrates an exploded perspective view of a device according to various embodiments.

With reference now to FIGS. 1A and 1B, a device 100 for establishing a distal femoral resection position in a total knee arthroplasty procedure can comprise a tibial support 101 and a femoral resection guide 102. A tibial support can further comprise a femoral resection guide alignment arm 103 and one or more pin bores 104. Tibial support 101 may have a unitary construction or a modular construction, as described in greater detail below.

A tibial support 101 can comprise a tibial support body 105 in the shape of a rectangular plate with an anterior face 105 and a posterior face 106. Tibial support 101 can be configured for attachment to an anterior aspect of a proximal tibia, such as by engaging one or more intramedullary pins placed in the anterior face of the proximal tibia in the course of performing a proximal tibial resection. The configuration of the tibial support 101 and/or tibial support body 105 may be suitable to provide stable engagement of a plurality of pins and support for a femoral resection guide attached to the tibial support, with the dimensions and configuration of the tibial support body 105 of suitable size and shape to engage pins placed in a tibia in any of a variety of tibial pin configurations, including various positions, spacings, and angles relative to one another and/or an axis of the tibial support 101 or device 100. For example, a tibial support body 105 thickness may be suitable to eliminate or substantially reduce rotation of tibial support 101 in a direction perpendicular to the plane of the anterior face 106. In an exemplary embodiment, tibial support body 105 may comprise a substantially rectangular body with a width of approximately 35 mm, a height of approximately 18 mm, and a thickness of approximately 10 mm. However, any of a variety of shapes and configurations of a tibial support may be used in accordance with the present disclosure without affecting the suitability of the tibial support to be attached to a tibia or perform the functions of a tibial support 101 and device 100 described in greater detail herein.

In various embodiments and as described briefly above, a tibial support 101 may comprise one or more pin bores 104. The pin bores 104 may be disposed through the tibial support body 105 from the anterior face 106 to the posterior face 107 and may be suitable to allow tibial support 101 to removably engage intramedullary pins placed in the tibia. Pin bores 104 may extend through the tibial support body 105 at an angle that is substantially perpendicular to a reference feature such as the anterior face 106 of the tibial support, or pin bores 104 may be at an angle to the anterior face 106, as described further below.

A pin bore 104 may be suitably dimensioned to permit the pin bore to receive the shaft of an intramedullary pin used in an orthopedic surgical procedure, such as a 75 mm×3.2 mm trocar tipped drill pin. For example, a pin bore 104 may have a diameter of 3.28 mm to allow the pin bore 104 to receive the shaft of a 3.2 mm diameter pin within the bore and permit tibial support 101 to slide freely over the pin with sufficiently precise tolerances to substantially minimize movement or play of the tibial support 101 about the pin. Various other pin diameters may be used, and pin bores may be of any suitable complementary size compatible with intramedullary pins used in a surgical procedure.

Likewise, a tibial support may be configured with a plurality of pin bores in a pin bore configuration suitable to permit the tibial support to slide over a plurality of pins inserted in a tibia in a tibial pin configuration. Any of a variety of pin bore configurations are possible to adapt a device in accordance with the present disclosure to various tibial pin configurations that may be used in standard procedures for preparing a tibia for a total knee replacement.

For example, a tibial support may comprise pairs of pin bores configured to engage pairs of pins placed in a tibia. Pin bores 104 and/or pairs of pin bores 104 may be configured with various spacings, positions, anterior-to-posterior angles relative to the tibial axis, and the like. For example, tibial support 101 comprises three pairs of pin bores 104. The placement of each pin bore 104 in a pair may be configured at a predetermined angle relative a reference feature or another portion of the device 100, such as femoral resection guide slot 140 or femoral resection guide alignment arm 102. Expressed differently, the configuration of pin bores 104 in tibial support 101 may provide device 100 with a predetermined femoral resection guide slot angle relative to a tibial resection plane. For example, pin bores 104 may be configured to be parallel to femoral resection guide slot 140 in an assembled device 100 with femoral resection guide 102 coupled to femoral resection guide alignment arm 103. Likewise, a pair of pin bores may be configured with a pin bore spacing, such as 20 mm from center to center, that may be compatible with the spacing of pins installed in a patient's tibia during a tibial resection step of a total knee replacement procedure. As explained further below, the tibial pin configuration in a tibia may provide a reference to the tibial resection plane, thereby enabling device 100 to effectively reference the tibial resection plane for purposes of establishing the distal femoral resection position using the devices and methods of the present disclosure.

In various embodiments, each pair of pin bores 104 may further provide different pin bore angles through tibial support body 105 relative to the plane of anterior face 106. Various bore angles may be used to provide a predetermined or desired alignment of device 100 relative to a patient's tibial axis. For example, each bore 104 of an upper bore pair may be oriented substantially perpendicular (or zero degrees downward, anterior to posterior) to the plane of anterior face 106, while each bore 104 of a middle bore pair may be angled three degrees downward (anterior to posterior) from perpendicular to anterior face 105, and each bore 104 of a lower bore pair may be angled seven degrees downward (anterior to posterior) from perpendicular to anterior face 106. With such an embodiment, the middle bore pair may be selected for attachment of tibial support 101 to pins inserted into the tibia at a downward three degree angle (anterior to posterior, relative to a plane transverse to the tibial axis) to provide substantial alignment of the plane of anterior face 106 of tibial support 101 (and likewise alignment of device 100) with the tibial axis). Other configurations and angles of pin bores may be used for tibial support 101, and pin bore configurations and angles may be provided and/or selected based on tibial pin configurations commonly used in various tibial resection devices such as guides or jigs that may be used to perform a tibial resection according to standard methods known to a person of skill in the art. Any suitable configuration of pin bores in a tibial support may be used and is within the scope of the present disclosure.

As described in greater detail below, the pin configuration used to attach a tibial resection guide or jig to a proximal tibia during performance of a proximal tibial resection may have a known relationship with the orientation of a tibial resection guide slot and the resultant resected tibial surface orientation produced using the tibial resection guide. The pins left in the tibia may then provide a suitable attachment for a tibial support of a device disclosed herein, further providing a reference to the orientation of the resected tibia. The tibial pins can be used as a reference for performing a femoral resection and can facilitate establishing a position of a distal femoral resection guide. The orientation of a resected surface of a distal femur can thereby be provided with a desired or predetermined relationship to the orientation of the resected tibial surface to establish a desired prosthetic gap. For example, a device such as device 100 may be suitable to provide an alignment of a femoral resection guide slot oriented to provide a resected femoral surface that is substantially coplanar with resected tibial surface, based on attachment and reference to tibial pins placed in the proximal tibia during the tibial resection and used to attach the tibial support 101 of device 100 to the tibia.

In various embodiments, tibial support 101 may comprise femoral resection guide alignment arm 103. Alignment arm 103 may be configured to extend from tibial support 101 at a predetermined angle. For example, alignment arm 103 may be configured to extend from tibial support 101 at an angle that is substantially orthogonal to a plane defined by the center of a pair of pin bores 104 in anterior face 106 and a line orthogonal to anterior face 106. An alignment arm may be integral to tibial support 101 or removably attached to tibial support 101, and in either way configured to provide rigid support for a femoral resection guide attached to tibial support 101. Alignment arm 103 may be integral to tibial support 101 and comprise an arm with a substantially rectangular cross section with an anterior face that is substantially coplanar with anterior face 106 of tibial support body 105. For example, alignment arm 103 may have a width of approximately 6-7 mm and a thickness of approximately 2-3 mm, and may extend 35-40 mm from the top of tibial support 101. In various embodiments, alignment arm 103 may be aligned with a central axis of tibial support 101; however other positions and/or alignments are possible and within the scope of the present disclosure. As will be readily appreciated by a person of ordinary skill in the art, an alignment arm may have any of a variety of configurations, including various cross sections, lengths, angles, and positions with respect to a tibial support without affecting the ability of the support arm to perform the functions described in the present disclosure with respect to alignment arm 103.

An alignment arm 103 may comprise a coupling component slot 120 configured to receive alignment arm coupling component 121. Slot 120 may be an elongated slot through alignment arm 103 and extending a portion of the length of the arm 103. For example, slot 103 may have a width of approximately 3 mm and a length of approximately 28 mm. The elongated configuration of slot 120 can permit alignment arm to be attached to femoral resection guide 102 within a continuous range of distances defined in part by the length of slot 120. The adjustable distance with which tibial support 101 can be attached permits the position of femoral resection guide 102 to be adjusted axially relative to the position of tibial support 101 while maintaining a predetermined relationship with respect to an angle between the femoral resection guide 102 and the tibial support 101, as explained in greater detail herein.

In various embodiments and as illustrated in FIG. 1B, a tibial support 101 may comprise a tibial support cutout 111 in tibial support body 105 and a modular tibial support, insert 112 configured to be complementary to and removably inserted into tibial support cutout 111. For example, cutout 111 may be defined by a perimeter comprising walls disposed through the thickness of tibial support body 105 and substantially perpendicular to the plane of anterior face 106. Tibial support insert 112 can comprise a generally block-shaped device with perimeter walls configured to be complementary to cutout 111 and received by cutout 111 with a precise fit that substantially eliminates side-to-side, up-and-down, and rotational movement of insert 112 with respect to cutout 111. In the illustrated embodiment, insert 112 comprises a "U" shaped block with the base of integrally attached alignment arm 103 located between the upward oriented arms of the insert. In other embodiments, a tibial support may comprise a plurality of cutouts (e.g., multiple cutouts shown by dividing line 92), with each cutout configured to receive an insert (e.g., multiple inserts as shown by dividing line 94). For example, the base of an alignment arm may extend across the height of tibial support (e.g., bisecting the width of the tibial support), and a tibial support may comprise cutouts on either side of support body.

Insert 112 may have flanges configured to contact an anterior surface or edge of tibial support 101 and provide a positive stop for insertion of the insert 112 in cutout 111, preventing insert 112 from passing through cutout 111 and providing alignment of the anterior surface of insert 112 with the anterior surface of tibial support 101 on insertion to the positive stop provided by the flange. Other mechanisms for establishing and/or reversibly fixing the position of an insert with respect to a tibial support may be used, such as a pin, a set screw, a spring, a clip, or the like. Any of a number of configurations or mechanisms that may be used to establish the position of an insert with respect to a tibial support will be apparent to a person of ordinary skill and are within the scope of the present disclosure. A tibial support insert can comprise pin bores as described above. For example and as illustrated FIG. 1B, tibial support insert 112 comprises three pairs of pin bores 104.

In various embodiments, a plurality of inserts 112 may be provided for use with a device 100 comprising a tibial support 101 with a cutout 111. Each insert can be complementary to cutout 111, while each may have a different configuration of pin bores 104, such as different pin bore placements, diameters, angles, or the like. Likewise, in various embodiments wherein a tibial support comprises a plurality of cutouts, a plurality of sets of inserts may likewise provide various configurations of pin bores. The modular nature of a tibial support comprising one or more cutouts may facilitate compatibility of a single tibial support 101 and device 100 with a variety of pin placement configurations that may be used to perform a proximal tibial resection. For example, a proximal tibial resection step may be performed using various standard equipment and procedures, such as tibial resection guides or jigs provided by different prosthetic joint providers. A tibial resection step may rely on pinning the tibial resection guide to an anterior aspect of a proximal tibia to align and stabilize the guide for performing the tibial resection, followed by removal of the resection guide, leaving the tibial pins inserted. As described above, the pins remaining in the tibia after use of such a tibial resection guide may provide a known configuration and relationship to the orientation of the plane of the resected surface of the tibia (i.e., the tibial resection plane), thereby providing useful reference and attachment points for a device disclosed herein that may be used to establish a position of a femoral resection guide and provide a desired prosthetic gap.

Figure 2A:
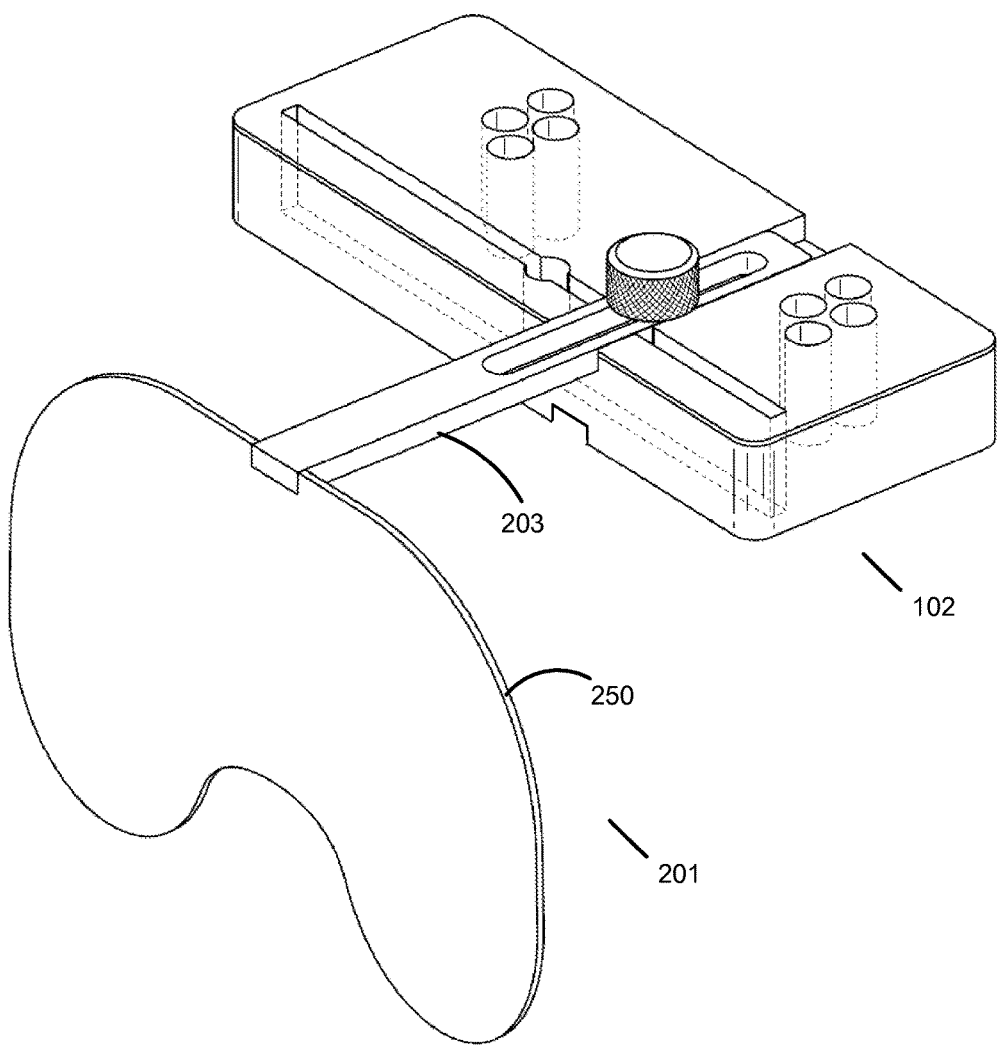
FIG. 2A illustrates a perspective view of a device according to various embodiments.
Figure 2B:
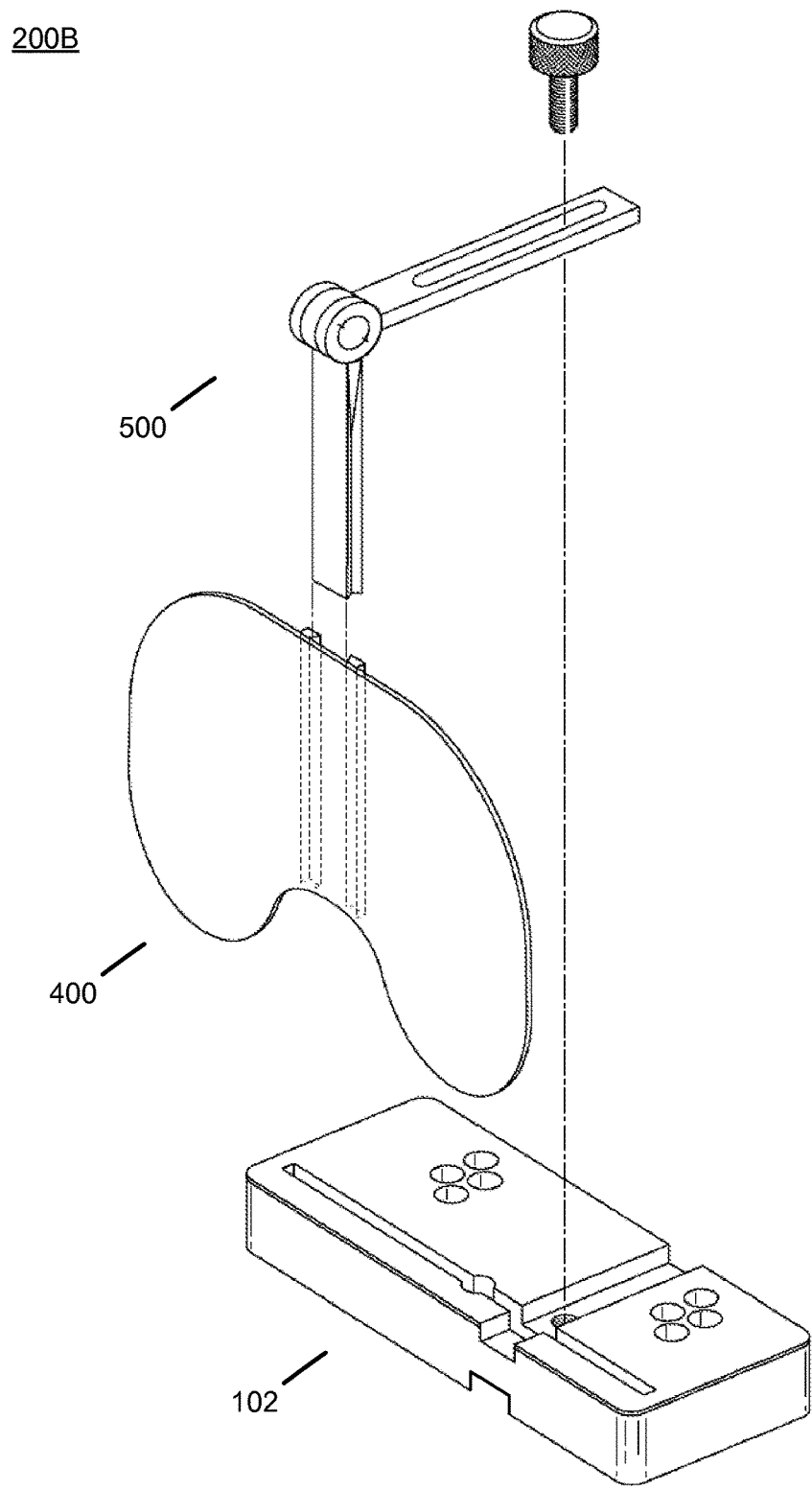
FIG. 2B illustrates an exploded perspective view of a device according to various embodiments.

In various other embodiments, a tibial support may be configured to reference the resected surface of a proximal tibial. With reference now to FIG. 2A, a device 200A comprising a tibial support 201 having a unitary construction is illustrated. Tibial support 201 may comprise a tibial surface contact plate 250 configured to contact the resected surface of a proximal tibia during a total knee arthroplasty procedure. Tibial surface contact plate 250 may be configured with a size and shape suitable to make contact with a substantial portion of the resected surface of a proximal tibia. Tibial support 201 may further comprise a femoral resection guide alignment arm 203. In various embodiments, alignment arm 203 may be integrally or detachably coupled to tibial surface contact plate 250. For example, in the embodiment illustrated in FIG. 2A, alignment arm 203 is integrally coupled to tibial surface contact plate 250 near an anterior edge (i.e., alignment arm 203 and tibial surface contact plate 250 have a unitary construction) and adjustably coupled to femoral resection guide 102. In various other embodiments and as illustrated in FIG. 2B, a device 200B comprising a tibial support with a detachably coupled alignment arm may comprise a tibial surface contact plate such as transverse surface contact plate 400 and an alignment arm such as modular adjustable angle alignment arm 500, described in greater detail below with reference to FIGS.

Figure 5:
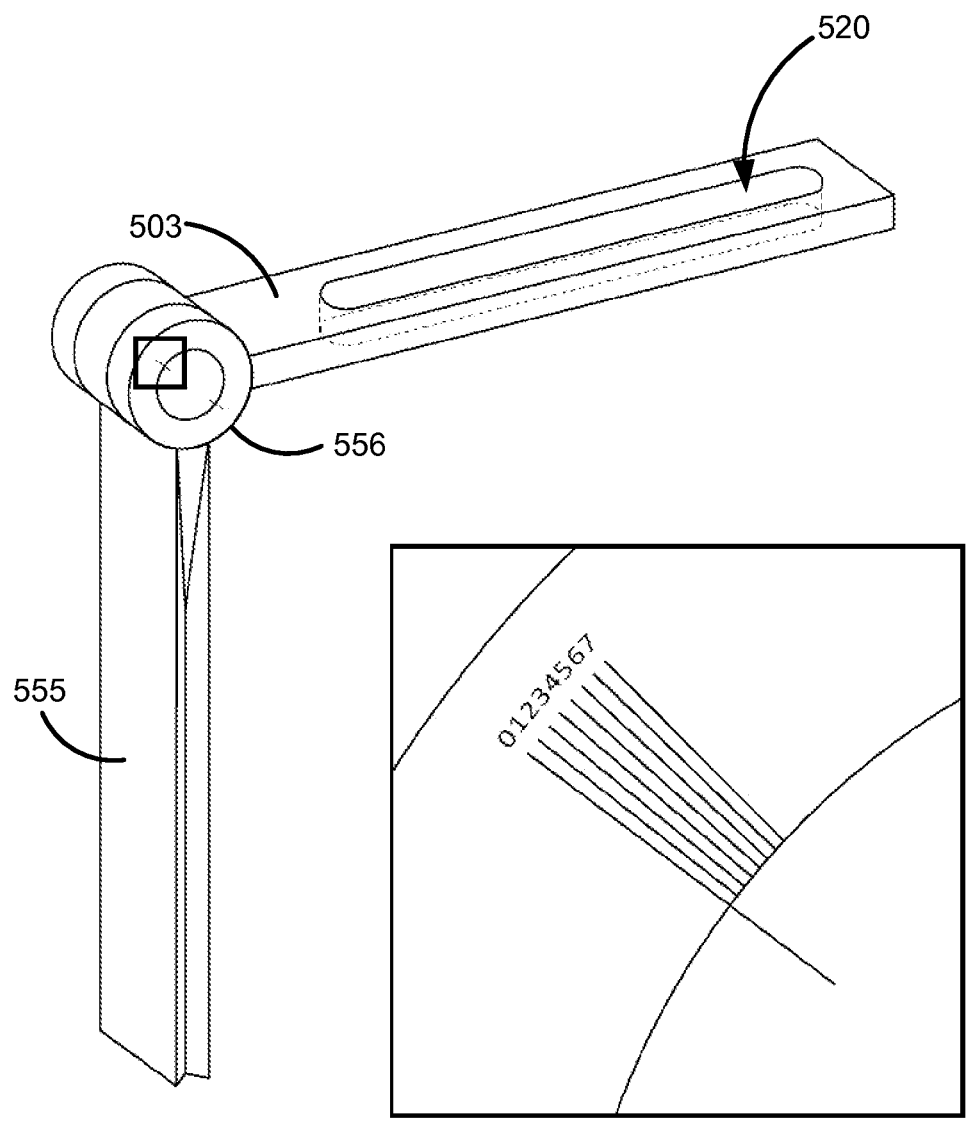
FIG. 5 illustrates a perspective view of an adjustable angle alignment arm according to various embodiments.

4A-4C and FIG. 5, respectively. Adjustable angle alignment arm 500 may be adjustably coupled to femoral resection guide 102. In various embodiments and as described elsewhere herein, an alignment arm such as alignment arm 203 or 500 is configured to provide a predetermined or adjustable alignment of a femoral resection guide 102 relative to the plane of contact plates 250 or 400 and/or the plane of a resected proximal tibia.

Figure 4A:
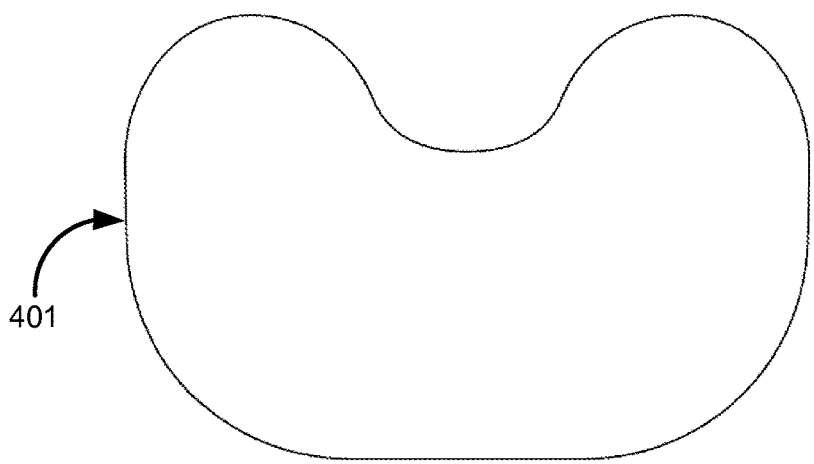
FIGS. 4A-4C illustrate views of a resected transverse surface contact plate according to various embodiments.
Figure 4B:
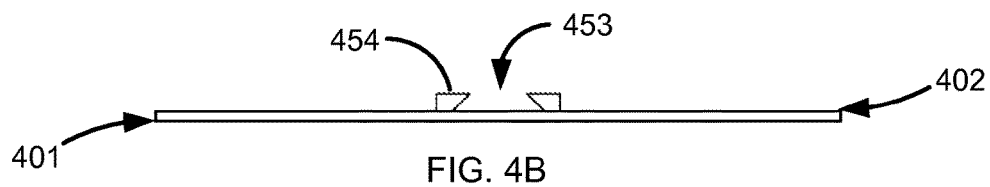
Figure 4C:
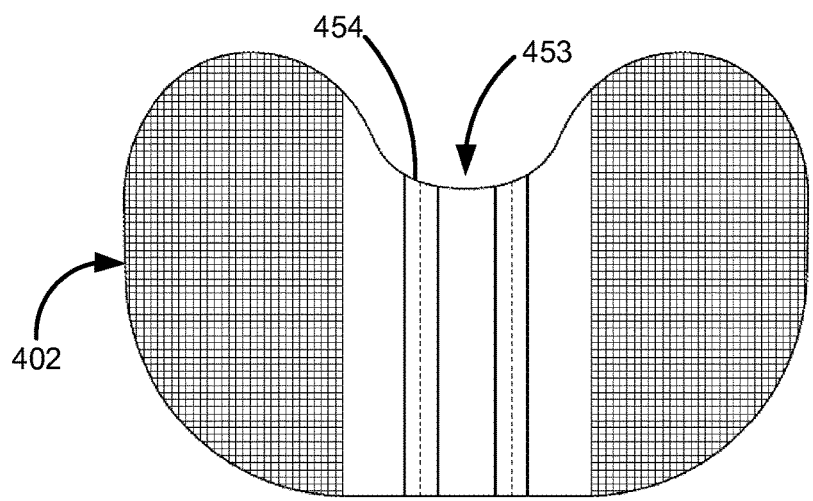

In various embodiments, an alignment arm may be configured to provide an adjustable angle between the plane of a transverse surface contact plate serving as a tibial surface contact plate and femoral resection guide 102. With reference now to FIG. 5, a modular adjustable angle alignment arm 500 is shown. Modular adjustable angle alignment arm 500 may comprise an alignment arm portion 503 with a coupling component slot 520. Alignment arm portion 503 may be hingedly connected to attachment arm 555 by hinge 556. Attachment arm 555 may comprise a cross sectional profile that is complementary to a receiving slot in a transverse contact plate 400 (FIGS. 4A-4C). For example, attachment arm 555 may comprise a double dovetail cross section that may be slidably inserted into dovetail slot 453 of transverse surface contact plate 400. The length and/or cross sectional profile of attachment arm 555 may be configured to provide a positive stop for insertion based on a change from a complementary cross section to, for example, a square or other cross section non-complementary to the channel into which attachment arm 555 may be inserted. This may prevent contact between a posterior end of attachment arm 555 and soft tissues in the back of a knee. Alternatively, the receiving channel may comprise a positive stop near a posterior aspect of the channel. A double dovetail cross section may permit arm 500 to be reversibly inserted into dovetail slot 453. Hinge 556 may be configured with a locking adjustment mechanism such as a spring and detents to provide positive and stable adjustment to various positions corresponding to known angles between attachment arm 555 and alignment arm portion 503. The locking adjustment mechanism of the hinge may be actuated, for example, by lateral or axial tension, enabling a surgeon or technician to rapidly adjust the hinge between various predetermined angles. Lateral faces of hinge 556 may be marked with an angle indicator showing the angle to which the hinge is set, for example 0-7 degrees of anterior-posterior slope relative to transverse contact plate 400 (i.e., corresponding to 90-97 degrees actual angle of arm 500 between attachment arm 555 and alignment arm portion 503). Hinge 556 may have a range of motion greater than 180 degrees. Hinge 556 may also have two sets of angle indicator markings for two general positions of alignment arm portion 503 relative to attachment arm 555 (e.g., ~90 degrees and ~270 degrees) on each lateral face of hinge 556. Two sets of angle indicator markings on each face of hinge 556 may facilitate reversible use of arm 500 and setting and/or determining the angle to which hinge 556 is set from either side of the device. Reversibility may facilitate convenient handling by a surgeon or operating room technician.

With reference again to FIGS. 1A and 1B, device 100 may further comprise femoral resection guide 102. Femoral resection guide 102 may comprise a guide body 135 in the shape of a rectangular plate with an anterior face 136 and a posterior face 137. For example, guide body 135 may comprise a substantially rectangular body with a width of approximately 63 mm, a height of approximately 25 mm, and a thickness of approximately 10 mm. Femoral resection guides with other dimensions and/or other shapes may also be configured with the various features of femoral resection guide 102 illustrated in FIGS. 1A and 1B and described below and are included within the scope of the present disclosure.

In various embodiments, a femoral resection guide may comprise an alignment arm receiving channel or slot. For example, in the illustrated embodiment, femoral resection guide 102 comprises alignment arm receiving channel 138 in anterior face 136. In addition, guide 102 further comprises a second alignment arm receiving channel 139 in posterior face 137. As used in reference to the femoral resection guide, the terms "anterior face" and "posterior face" are used merely to distinguish the two sides of guide 102, and the two alignment arm receiving channels permit each of anterior face 131 and posterior face 132 of guide 102 to reversibly engage alignment arm 103. Reversible engagement may facilitate use of a single device 100 with both right and left legs, as described in further detail below.

Alignment arm receiving channels 138 and 139 may be defined by parallel side walls substantially orthogonal to and channel bottoms that are substantially coplanar with the plane of anterior face 136 and posterior face 137. Alignment arm receiving channels 138 and 139 may span the height of femoral resection guide 102, with each end of channels 138 and 139 being open and configured to receive an alignment arm such as alignment arm 103. Channels 138 and 139 may offset (i.e., located off-center with respect to the length of resection guide body 130) and in the same vertical plane oriented orthogonally to anterior face 136 and posterior face 137, thereby providing an anterior channel configuration that is mirrored by a posterior channel configuration. The mirrored channel configuration and capacity of guide 102 for reversible engagement to alignment arm 103 provides for similar alignment of device 100 with a right or a left knee. However, other configurations are possible, and an alignment arm receiving channel may be located in any suitable position with respect to a femoral resection guide, including both centered and offset positions.

The dimensions of receiving channels 138 and 139 may be configured to be complementary to the dimensions of alignment arm 103 such that alignment arm 103 may freely slide reciprocally within channels 138 and 139 to provide axial adjustment of the distance between tibial support 101 and femoral resection guide 102. Receiving channels 138 and 139 may likewise be configured to permit alignment arm 103 to lift and/or rotate in and out of the channels when aligned and when not secured to femoral resection guide 102 by alignment arm coupling component 121. Moreover, the dimensions may further be suitable to substantially reduce rotational movement of alignment arm 103 within a plane substantially similar to that defined by anterior face 136 or posterior face 137. In this manner, the configuration of alignment arm receiving channels 138 and 139 and alignment arm 103 are suitable to produce a stable, predetermined alignment between tibial support 101 and femoral resection guide 102 via insertion of alignment arm 103 in one of alignment arm receiving channels 138 or 139, followed by attachment of alignment arm 103 to femoral resection guide 102, described in more detail below.

In various other embodiments, a femoral resection guide arm receiving slot may comprise a slot disposed through a femoral resection guide body, rather than an open channel located in the anterior or posterior surface of the femoral resection guide body. For example, a guide arm receiving slot may be a bored or machined passage through a guide body, rather than a channel located in a face of the guide body. Various slot cross sections may be suitable, including round cross sections that may permit axial rotation of a femoral resection guide about an inserted alignment arm, or non-circular cross sections, such as elliptical, triangular, square, rectangular, or irregular cross sections.

Likewise, an alignment arm may comprise any suitable corresponding cross section complementary to a bored or machined femoral resection guide arm receiving slot. In such embodiments, a coupling component such as a set screw may be used to secure the position of an alignment arm within and receiving slot. Similarly, a tibial support and alignment arm may be configured to be removably attached to one another in a manner similar to that described above with respect to a femoral resection guide. Any of a variety of alignment arm configurations and attachment mechanisms to a femoral resection guide and/or a tibial support may be suitable to provide axial adjustment of the position of the femoral resection guide with respect to a tibial support attached to a proximal tibia and also provide a predetermined angle of the resection guide with respect to the tibial support, and any device configuration suitable to perform the above functions is within the scope of the present disclosure.

A tibial support alignment arm may be attached to a femoral resection guide using a coupling component configured to reversibly secure a tibial support alignment arm to a femoral resection guide. As described briefly above, device 100 may comprise a coupling component such as coupling component 121. Coupling component 121 may comprise, for example, a knurled knob with a threaded shaft configured to be inserted through alignment arm slot 120 and threadedly engage a complementary threaded bore in femoral resection guide 102. Femoral resection guide 102 may comprise a complementary threaded bore 122 configured to receive coupling component 121. Threaded bore 122 may be located in the bottom of channels 138 and 139 and may be oriented substantially orthogonally to the plane defined by the bottom of channels 138 and 139. Coupling component 121 may be configured to provide sufficient mechanical force to secure the position of alignment arm 103 within channel 138 or 139, preventing proximal or distal movement of alignment arm 103 within the channel and likewise retaining alignment arm within the channel.

The surfaces of alignment arm 103 and channels 138 and 139 may be substantially smooth machined surfaces, and coupling component 121 may prevent alignment arm 103 from sliding within channels 138 and 139 by operating to apply sufficient compressive force on alignment arm 103. In other embodiments, an alignment arm and alignment arm receiving channels may comprise detents or other complementary features to provide a range or array of positive alignment positions. Likewise, other attachment mechanisms and components may be used to reversibly secure an alignment arm to a resection guide. For example, in various embodiments, a cammed or other quick-release type mechanism that relies on a lever or similar a device for actuation may be used. In various embodiments, a coupling component may comprise a head, handle, or actuator that may fit through slot 120 when in a first (i.e., open) orientation so that alignment arm 103 may be inserted into one of channels 138 or 139 when the coupling component is attached to femoral resection guide 102. A partial manipulation of the coupling component mechanism (e.g., a twist) may retain arm 103 in the channel, with actuation to a second (i.e., closed) orientation further securing the proximal-distal position of alignment arm 103 in the channel. A variety of mechanical attachment mechanisms and devices will be well known to a person of ordinary skill in the art and may be substituted for illustrated coupling component 121.

In various embodiments, femoral resection guide 102 may be configured for attachment to an anterior aspect of a distal femur. Femoral resection guide 102 may comprise a plurality of femoral resection guide pin bores 134. Pin bores 134 may be disposed through femoral resection guide body 135 between and substantially orthogonal to anterior face 136 and posterior face 137. Femoral resection guide pin bores 134 may be configured similarly to tibial support pin bore 104 and suitable to receive the shaft of a intramedullary pin used in an orthopedic surgical procedure, such as a trocar tipped drill pin. Femoral resection guide 102 may be attached to an anterior aspect of a distal femur by insertion of intramedullary pins through pin bores 134 into the exposed anterior surface of a distal femur.

Femoral resection guide 102 may comprise a plurality of pairs of pin bores 134. Each pair of pin bores may be configured to provide stable attachment of the femoral resection guide to the distal femur. Each of the pin bores of a pair may be located in the upper portion of the femoral resection guide body and disposed near opposite ends of the guide body or separated by a pin bore spacing of, for example, 36 mm. Any suitable pin bore spacing compatible with attaching a device to an anterior aspect of a distal femur may be used. Each pair of pin bores may be disposed in the guide body with a predetermined alignment with a femoral resection guide slot 140 located in the lower portion of the femoral resection guide body, such as a substantially parallel alignment.

In the illustrated embodiment, four pairs of pin bores are provided. Each pair may be configured in a position relative to an adjacent pair that permits the femoral resection guide to be moved vertically in a predetermined increment, such as a 2 mm increment, between pin bore pairs. Each pair may be staggered laterally from the adjacent pin pair to accommodate the bore diameter while providing the desired vertical adjustment increment. Other pin bore configurations may be used to provide different increments and/or a different number of increments of femoral resection guide adjustment relative to a pair of pins placed in a femur. As described in greater detail below, the pin bore configurations described above permit the location of the femoral resection guide to be precisely adjusted in predetermined proximal-distal increments in relation to the longitudinal axis of the limb following placement of intramedullary pins in a distal femur while maintaining a predetermined alignment with the femoral resection guide slot 140. Such adjustment may be useful in a femoral resection procedure, for example, to provide for additional distal femoral bone tissue to be removed following an initial cut, or to allow repositioning of the guide after femoral pin insertion to allow a more conservative initial resection.

Femoral resection guide slot 140 may comprise a slot disposed between the anterior face 136 and the posterior face 137 of femoral resection guide 102. Slot 140 may be defined by walls oriented substantially orthogonally to the plane of anterior face and the posterior face, with horizontal walls extending a substantial portion of length of the femoral resection guide body and defining a slot width suitable to accommodate the blade thickness of reciprocating or oscillating saw that may be used for to resect bone. For example, in the illustrated embodiment, slot 140 is approximately 59 mm long (in a 64 mm long femoral resection guide body), with a slot width of approximately 1.5 mm. The ends of slot 140 may be defined by substantially vertically oriented walls connecting the upper and lower horizontal slot walls. In various embodiments, slot 140 may further comprise a pin bore 141 disposed in the center of the slot. Pin bore 141 may be configured to receive a standard intramedullary pin for use in ascertaining the position of femoral resection guide 102 relative to the distal end of a femur, as described in more detail below.

The slot dimensions may be suitably configured to guide resection of the distal end of a femur using a saw blade inserted through the slot, with the slot width configured to be complementary to or compatible with the thickness of a saw blade, whereby the saw blade can oscillate freely but is substantially prevented from rotating within the slot about an axis parallel to the length of the slot, thereby providing guidance for a substantially planar femoral resection. Likewise, the slot length may be suitable to span a sufficient width of a distal femur so that a saw operated using the slot to guide the blade can be used to resect the entire distal end of the femur. A femoral resection guide may comprise different slot lengths and/or slot widths, depending, for example, on the application and femur size, the type of surgical equipment to be used, and the like.

A femoral resection guide slot such as slot 140 may be configured with a slot orientation having a predetermined relationship to another portion of a device. For example, the orientation of the longitudinal axis of a femoral resection guide slot may be substantially parallel to an axis defined by a line bisecting a pair of tibial support pin bores, or the orientation of the longitudinal axis of a femoral resection guide slot may be substantially perpendicular to the orientation of an alignment arm and an alignment arm receiving channel or slot. In this manner, the position and orientation of the femoral resection guide and the femoral resection guide slot may be established with a predetermined orientation relative to, for example, a pair of intramedullary pins placed in a tibia, thereby establishing the position and orientation of the plane of the resected surface of the distal femur relative to the plane of the resected surface of the proximal tibia.

In various embodiments, a femoral resection guide may comprise femoral resection guide cutouts suitable to receive femoral resection guide inserts, such as those described above with respect to a tibial support. As previously described for the tibial support, one or more femoral resection guide cutouts in the femoral resection guide body may be provided so that the device can be modularly configured with a greater variety of pin bore configurations, thereby accommodating various pin sizes, pin configurations, pin placements relative to a resection guide slot, distal femur sizes, and the like.

A device for establishing a distal femoral resection position in a total knee arthroplasty may comprise a metal material such as surgical stainless steel. Alternatively, in various embodiments comprising a modular tibial support and or femoral resection guide, a tibial support insert or a femoral resection guide insert may comprise a polymeric material, while the other portions of the device such as the portions of the tibial support body and the femoral resection guide body that receive the inserts may comprise surgical stainless steel. For example, a tibial support insert or a femoral resection guide insert may be constructed of a thermoplastic polymer such as polyether ether ketone, polyetherimide, or other similar polymer materials, such as polycarbonate, polystyrene, ABS, acrylics, polyimide, polyethersulfone, polyphenylsulfone, polymethylmethacrylate, or any other bio-compatible injection moldable polymer. In various other embodiments, an entire device may comprise polymer materials.

A device comprising modular components such as tibial support inserts and femoral resection guide inserts manufactured from a polymeric material may provide for decreased costs of manufacture and use of such a device. In such embodiments, the primary device comprising the tibial support and femoral resection guide may be manufactured from surgical stainless steel and reused repeatedly, while the inserts used to adapt the primary device to various surgical applications and provide compatibility with various third party tibial resection jigs may be more economically manufactured from polymeric material and may further be single use or disposable. In this manner, a modularly configured device using disposable polymeric inserts might serve to decrease the number of durable medical instruments a hospital or other surgical institution would need to acquire and maintain in inventory. However, tibial support inserts and/or femoral resection guide inserts may also be manufactured from metal such as surgical stainless steel and may be reusable. Alternatively, an entire device may be manufactured from one or more polymeric materials and be disposed of after a single use. Any combination of appropriate materials suitable to be used for the manufacture and application of the devices described herein are within the scope of the present disclosure.

In various embodiments, a kit for establishing a distal femoral resection position or a proximal tibial resection position in total knee arthroplasty procedure is provided. A kit may comprise a device for establishing a distal femoral resection position in a total knee arthroplasty procedure, a transverse surface contact plate, and one or more femoral tibial spreaders. A kit may further comprise tibial support inserts and/or femoral resection guide inserts that may be packaged and supplied separately from the device for establishing a distal femoral resection position. A kit may also comprise a device for establishing a proximal tibial resection and various inserts that may used in such a device. A kit may also comprise an adjustable angle alignment arm. A kit may also comprise an optional angle validation tool for determining the anterior-posterior slope of a tibial resection.

Each device for establishing a distal femoral resection position in a total knee arthroplasty procedure can comprise several components, such as a tibial support, a femoral resection guide, an alignment arm, and an alignment arm coupling component. In various embodiments, each device may further comprise one or more tibial support inserts and/or one or more femoral resection guide inserts. For example, a kit in accordance with various embodiments can comprise a device such as device 100 (FIGS. 1A and 1B), device 200A (FIG. 2A), or device 200B comprising devices 400 (FIGS. 4A-4C) and 500 (FIG. 5) plus a femoral resection guide such femoral resection guide 102 (FIG. 1).

Figure 3:
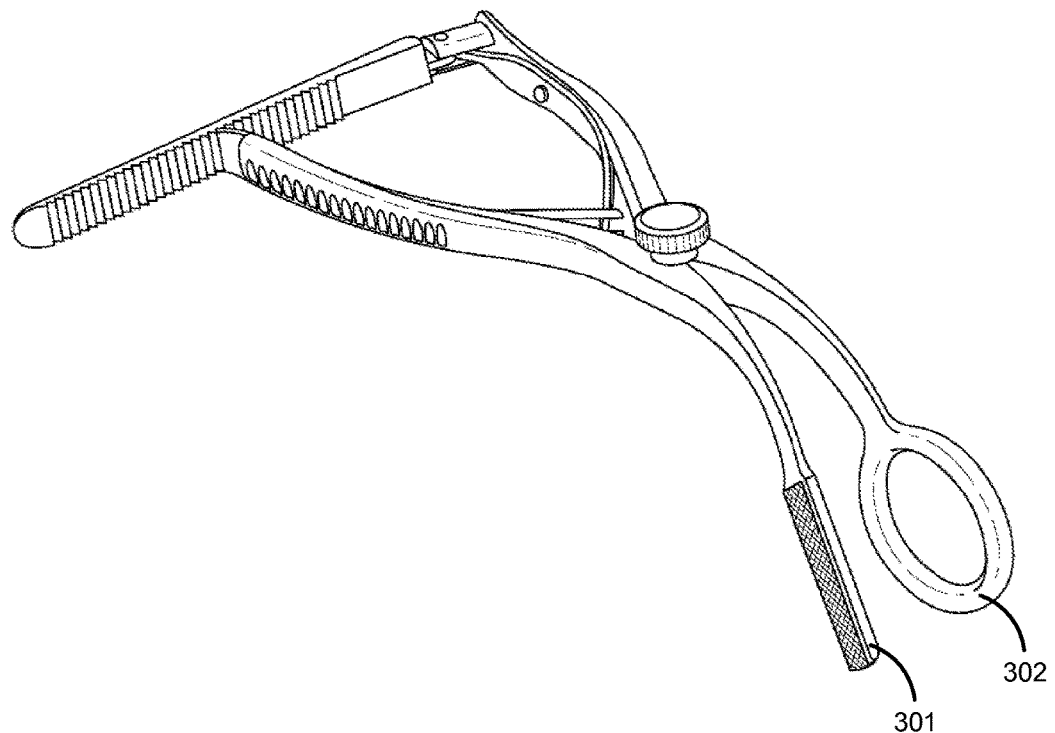
FIG. 3 illustrates a perspective view of a femoral tibial spreader according to various embodiments.

A kit may further comprise a pair of joint distraction devices. The pair of joint distractions devices may comprise a lateral joint distraction device and a medial joint distraction device, such as a medial femoral tibial spreader and a lateral femoral tibial spreader. The medial femoral tibial spreader may be configured to provide tension on a medial collateral ligament in an exposed knee during a total knee arthroplasty, and a lateral femoral tibial spreader may be configured to provide tension on a lateral collateral ligament. With reference to FIG. 3, a femoral tibial spreader 300 in accordance with various embodiments is illustrated. Femoral tibial spreader 300 may have a handle length of about 100 mm and an overall arm length of about 55 mm, with an angle of about 45 degrees between the handle and arms. Femoral tibial spreader 300 may comprise a distal pad, such as rectangular distal pad 301 with a serrated surface configured to engage a textured surface of a transverse surface contact plate, and a proximal ring 302 configured to engage a distal end of an intact femur.

In various embodiments, proximal ring 302 of femoral tibial spreader 300 may comprise an elongated or elliptical ring, with a long axis of the ring oriented substantially parallel to the long axis of the distal pad (i.e., approximately parallel to the axis of the supporting arm of the femoral tibial spreader). The rectangular distal pad may have a length of about 30-40 mm and a width of about 8-12 mm. The elliptical proximal ring may have an outside diameter of about 30-40 mm on the long axis, an inside diameter of about 22-32 mm, and an outside diameter on the short axis of about 15-25 mm. Other ring shapes and dimensions are possible, however, including irregular, non-Euclidean, and non-planar geometries, and a proximal ring of a medial femoral tibial spreader may have any configuration suitable to engage the medial condyle of a distal femur, while a proximal ring of a lateral femoral tibial spreader may have any configuration suitable to engage the lateral condyle of a distal femur. An open ring configuration may provide more secure engagement of various condylar features than a pad configured as a continuous, planar plate. The proximal surface of the proximal ring may have any suitable finish to facilitate stable engagement of the distal femur, including, for example, both smooth and serrated or otherwise textured finishes. In various embodiments, a tensor/spreader may be used, and a device such as that illustrated in FIG. 3 and described above may further include a calibrated tension measuring component.

A kit may also comprise a transverse surface contact plate. With reference to FIGS. 4A-4C, a transverse surface contact plate 400 can comprise a thin, flat plate configured with a kidney-shaped surface area profile with a size and shape similar to that of a typical transverse section of a proximal tibial or distal femur. Plate 400 may serve to protect a resected tibial or femoral surface from focused pressure that may be exerted by a femoral tibial spreader or other instrument during distraction of a knee. A plate may be manufactured from surgical stainless steel and be sufficiently thick to resist flexion or deformation under pressure applied, for example, by an instrument such as a femoral tibial spreader. A plate may comprise a substantially smooth surface 401 opposite a serrated or textured surface 402. Plates that are substantially smooth on both sides and plates textured on both sides are likewise within the scope of the present disclosure. Similarly, various patterns and degrees of texture may be used for a plate and within the scope of the present disclosure.

Surface 402 may further comprise a dovetail channel 453 defined by walls 454. Dovetail channel 453 may be configured to slidably receive a support arm with a complementary dovetail (or double dovetail) cross section. Dovetail channel 453 may bisect surface 402. Other channel cross sections and configurations are possible and within the scope of the present disclosure. In various embodiments, a plate 400 need not comprise a dovetail slot, for example, for a procedure in which a device such as device 100 supported by pins in the anterior tibia will be used.

In use, plate 400 may be oriented with smooth surface 401 towards and contacting a resected surface of a proximal tibia or distal femur and textured surface 402 oriented away from the resected surface. The textured surface may provide traction for one or more femoral tibial spreaders that may be used to distract a knee. Dovetail channel 453 may slidably receive and provide support for a support arm with a complementary dovetail cross section such as adjustable angle alignment arm 500 illustrated and described with reference to FIG. 5.

Different sized plates with different surface areas may be provided to accommodate patients having a range of tibial or femoral cross section sizes. Furthermore, in various embodiments and as illustrated for device 200A and described with reference to FIG. 2A, a resected tibial surface contact plate such as plate 250 may comprise a portion of a tibial support and provide both protection of the resected tibial surface during distraction of the knee while in full extension and at the same time provide a reference surface for alignment of device 200A and femoral resection guide 102. Likewise, transverse surface contact plate 400 illustrated in FIG. 4 may be provided in various sizes compatible with a range of tibial or femoral cross section sizes.

Figure 6:
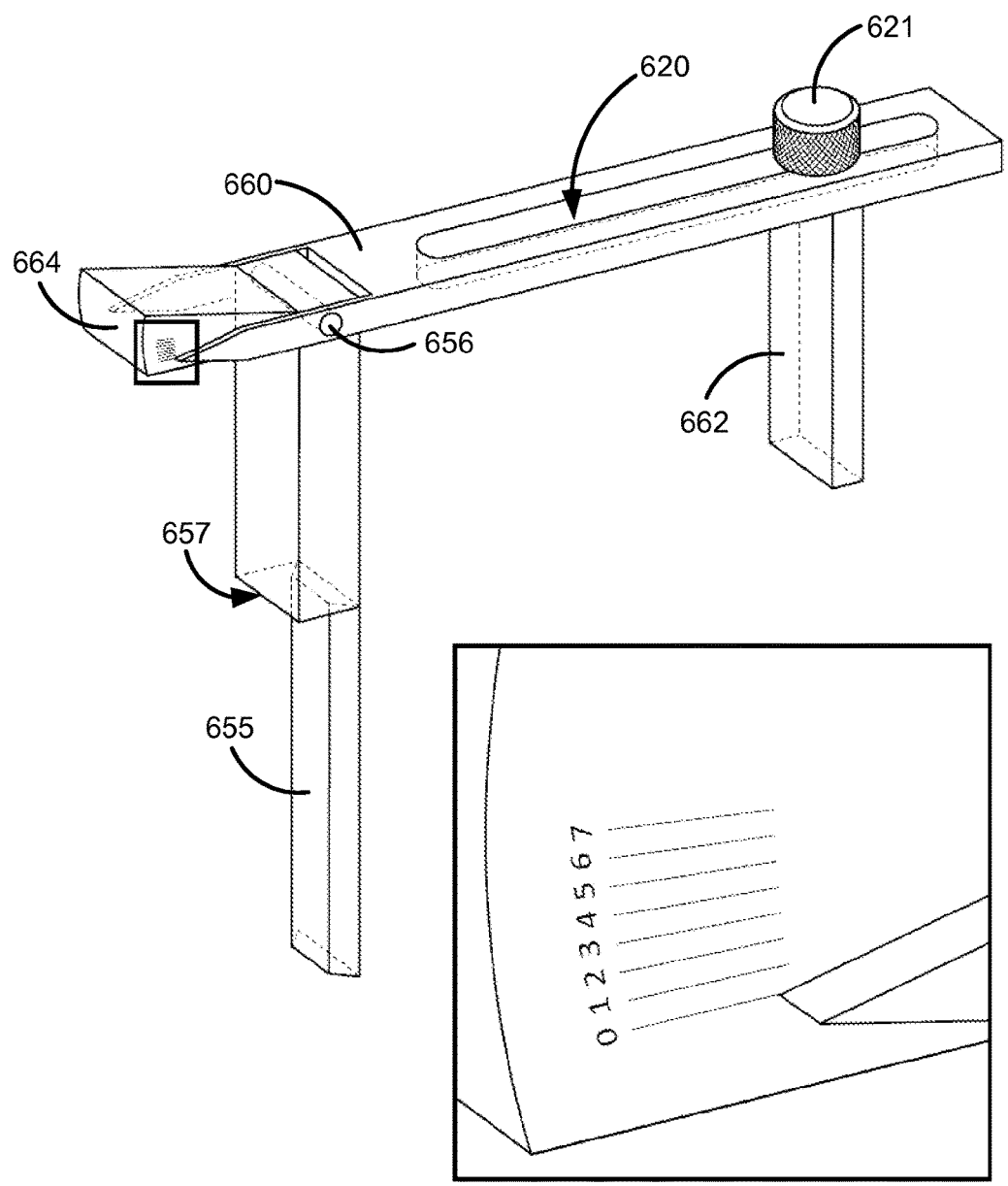
FIG. 6 illustrates a perspective view of an angle validation tool according to various embodiments.

A kit may also comprise an angle validation tool for determining the anterior-posterior slope of a tibial resection. An angle validation tool 600 in accordance with various embodiments is illustrated in FIG. 6. Angle validation tool 600 may comprise an attachment arm 655 with a cross sectional profile complementary to dovetail channel 453 of transverse surface contact plate 400 (FIG. 4). Attachment arm 655 may further comprise a transition to a rectangular cross sectional profile that may serve as a positive stop 657 for insertion of attachment arm 655. The length of attachment arm 655 positive stop 657 to hinge 656 may be a known distance, for example, 30 mm. A drop rod 660 may be hingedly connected to attachment arm 655 by hinge 656. Drop rod 660 may be have a length of 15-25 cm and may comprise a slot 620. A short leg 662 with a length corresponding to the length of attachment arm 655 between positive stop 657 and hinge 656 may be adjustably attached to drop rod 660 via a coupling device 621 inserted through slot 620. An angle measuring device 664 may be located adjacent hinge 656.

In use, angle validation tool 600 may be attached to transverse surface contact plate 400 applied to a resected proximal tibia. Attachment arm 655 is inserted into dovetail channel 453 to positive stop 657, which contacts the anterior portion of plate 400 aligned to the anterior surface of the tibial. The proximal-distal position of short leg 662 may be adjusted along slot 620 to a position opposite an anterior point of a patient's lower leg (i.e., the tibia). The end of short leg 662 is placed in contact with the leg, and angle measuring device 664 is used to determine the anterior-posterior resection angle, for example, between 0 and 7 degrees anterior-posterior downward slope.

Each component of a kit may be separately packaged, and each component may be selected for use in a surgical procedure based on various criteria such as the anatomy and condition of a patient, the prosthesis and other instrumentation to be used, surgeon preference, and the like.

In various embodiments, a method for establishing a distal femoral resection position to provide a prosthetic gap is provided. A method for establishing a distal femoral resection position can comprise establishing an axial position of a transverse resection with respect to the distal end of a femur, an alignment of a resection, or both. The method described herein is performed as part of a total knee arthroplasty procedure that may be performed in part using various standard techniques. The method disclosed is not intended to encompass the entire total knee arthroplasty procedure. The distal femoral resection position and prosthetic gap may be established for the knee in extension before the flexion gap is established, and the extension gap may be determined with reference to a resected proximal tibial. Furthermore, while the method described is intended to provide a method for preparing to perform a distal femoral resection with a desired prosthetic gap, the method may comprise establishing the position of a femoral resection guide without encompassing the step of performing the distal femoral resection.

Figure 7:
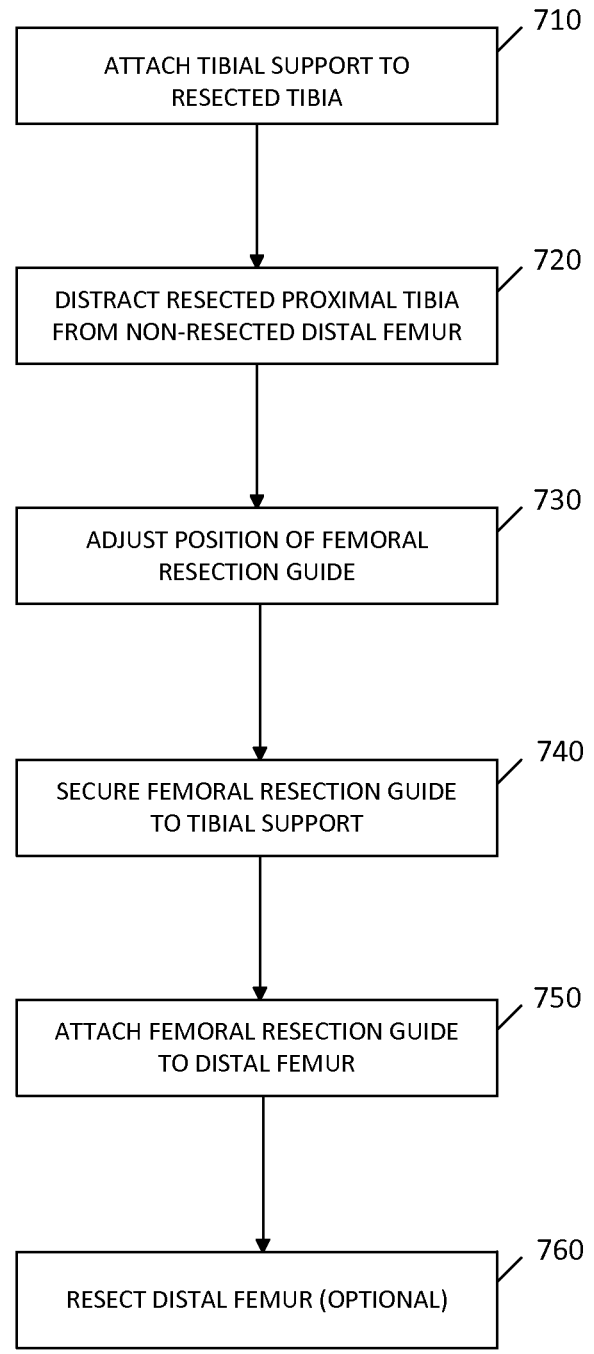
FIG. 7 illustrates a process for establishing a distal femoral resection position in a total knee arthroplasty procedure according to various embodiments'

With reference now to FIG. 7, a method 700 for establishing a distal femoral resection position may comprise the steps of: attaching a tibial support of a device for establishing a distal femoral resection position to a resected tibia 710; distracting a resected proximal tibia from a non-resected distal femur 720; adjusting a position of a femoral resection guide 730; securing the femoral resection guide to the tibial support 740; attaching the femoral resection guide to an anterior aspect of the distal femur 750; and optionally resecting the distal femur at the desired resection level using the femoral resection guide 760.

In various embodiments, method 700 comprises a step of attaching a tibial support of a femoral resection guide to a resected tibia 710. A tibial support may be attached to an anterior aspect of a proximal tibia by sliding the tibial support onto a pair of intramedullary pins previously inserted into an anterior aspect of a proximal tibia and used to stabilize a proximal tibial resection guide. The tibial resection guide (or jig) may be removed after the proximal tibia has been resected, leaving the intramedullary pins in place. In general, a tibial resection guide used to perform a tibial resection according to standard methods will have a specific pin configuration with a predetermined relationship relative to the resection guide and the resultant resected tibial surface. These specifications are generally known to the surgeon and/or described in detail in the technical specifications and surgical technique guide accompanying the tibial resection guide kit or apparatus.

In various embodiments, attaching a tibial support to a resected tibia may further comprise a step of selecting a tibial support and/or tibial support insert. A tibial support and/or tibial support insert combination may be selected for compatibility with the tibial resection guide pin configuration and tibial resection alignment, with the tibial support being selected to provide a desired predetermined alignment of an attached femoral resection guide to achieve a desired alignment between the resected surface of the proximal tibia and the resected surface of the distal femur resected in accordance with the methods disclosed herein.

In various embodiments comprising attachment of a tibial support to an anterior aspect of a resected proximal tibia, method 700 may further comprise a step of placing a transverse surface contact plate 715 in contact with the resected surface of the tibia. The contact plate may be placed in contact with the resected surface before or after attachment of the tibial support to the anterior tibia 710, and may be conveniently inserted in the joint space and placed in contact with the resected tibial surface while the knee is in flexion following the tibial resection. An appropriately sized contact plate may be selected from a plurality of plate sizes to provide maximum coverage and protection of the medullary tissue exposed at the resected surface without extending beyond the tibial cross section in a manner that might interfere with placing the leg in extension and performing subsequent surgical steps. For methods using a contact plate such as plate 400 (FIGS. 4A-4C) with a smooth and a textured surface, the smooth surface may be placed in contact with the resected tibial surface and the textured surface with dovetail slot 403 may be oriented toward the distal femur.

In various embodiments of method 700 that use a tibial support comprising a device such as device 200A illustrated in FIG. 2A, or device 200B illustrated in FIG. 2B (comprising devices 400 and 500 illustrated in FIGS. 4A-4C and 5, respectively), steps 710 and 715 are essentially performed simultaneously, as the tibial support comprises resected tibial surface contact plate 250 or transverse surface contact plate 400.

Following attachment of a tibial support and placement of a transverse surface contact plate, method 700 may further comprise a step of distracting the resected proximal tibia from the non-resected distal femur 720 with the knee in full extension. A pair of femoral tibial spreaders may be used to perform distraction. For example, a medial femoral tibial spreader may be used to tension the medial collateral ligament and a lateral femoral tibial spreader may be used to tension the lateral collateral ligament. The distal arms of each femoral tibial spreader may comprise a flat pad with a distal textured surface that contacts a textured surface of the transverse surface contact plate, while the proximal arms of each spreader may comprise an elongated ring that engages the native (non-resected) distal femoral condyles to provide stable tension on the ligamentous structures. Distraction step 720 may comprise applying even, balanced tension on the medial and lateral collateral ligaments and further ensuring that the knee is in full extension.

Following distraction step 720, method 700 may further comprise adjusting a position of a femoral resection guide 730. A femoral resection guide may be attached to an alignment arm of a tibial support, and the position of the femoral resection guide may be axially adjusted relative to a reference point on the distal end of the non-resected femur. The reference point may be the central distal femoral intracondylar notch. The position of the femoral resection guide may be adjusted for a desired transverse femoral resection position relative to the distal end of the femur by using the femoral resection guide slot and inserting a probe device such as a saw blade, resection estimating finger, flat finger, feeler, angel wing, bat wing, intramedullary pin (inserted in bore 141 located in slot 140), or the like through the guide slot and sliding the femoral resection guide axially on the tibial support alignment arm until the probe device abuts the valley of the central notch.

Adjusting a position of a femoral resection guide 730 may comprise various additional steps prior to completion of step 730. In various embodiments, a method 700 may further comprise steps of validating an angle of a tibial resection and/or establishing an angle of a distal femoral resection. For a method performed using adjustable angle alignment arm 500 (FIG. 5) in conjunction with transverse surface contact plate 400 (FIGS. 4A-4C) (i.e., device 200B illustrated in FIG. 2B), alignment arm 500 must first be installed in dovetail channel 403, the angle adjusted at hinge 556, and a femoral resection guide such as guide 102 (FIGS. 1A and 1B) attached to alignment arm portion 503. Adjustment of an angle of adjustable angle alignment arm 500 at hinge 556 may be useful to establish a desired anterior-posterior slope of a femoral resection relative to the plane of the resected proximal tibial surface, for example, to create a neutral femoral resection relative to a sloped tibial resection or to introduce flexion into the prosthetic joint by virtue of creating an anterior-posterior femoral resection slope that is at a downward angle relative to the tibial slope.

In various embodiments, the anterior-posterior slope of the tibial resection may be measured using angle validation tool 600 (FIG. 6) prior to insertion of adjustable angle alignment arm 500. Angle validation tool 600 may be used to determine the anterior-posterior slope of the tibial resection as described above with reference to FIG. 6. The angle measured using angle validation tool 600 may be used to adjust the angle of alignment arm 500, as described above. After the angle of hinge 556 has been set, the proximal-distal position of femoral resection guide can be established as described above relative to step 730.

After the position of the femoral resection guide is established in step 730, method 700 may further comprise securing the femoral resection guide to the tibial support 740. Securing the femoral resection guide to the tibial support may comprise inserting and/or tightening a coupling component configured to detachably couple the tibial support alignment arm to the femoral resection guide. With reference to FIGS. 1A and 1B, in addition to FIG. 7, step 740 may comprise tightening coupling component 121, such as the illustrated knurled knob. In accordance with various embodiments, securing the femoral resection guide to the tibial support 740 provides a predetermined alignment of a femoral resection guide slot with the resected tibial surface via the referencing the position of tibial pins (i.e., using device 100 (FIGS. 1A and 1B)) used to perform the tibial resection or via referencing the resected tibial surface itself (i.e., using devices 200A or 200B (FIGS. 2A and 2B)).

Once the position of the femoral resection guide has been established and secured relative to the tibial support and the distracted knee, the femoral resection guide may be attached to the anterior aspect of the distal femur 750. The femoral resection guide may be attached to the femur by placing intramedullary pins through a pair of pin bores in the femoral resection guide. Following placement of pins into the femur, the tibial support may be uncoupled from the femoral resection guide to permit flexion of the knee and/or access to the resection guide slot that is unobstructed by the alignment arm. For femoral resection guides comprising several pairs of pin bores that permit incremental adjustment of the proximal-distal position of the femoral resection guide, pinning the resection guide to the femur using an intermediate pin pair position permits the resection guide to be removed and replaced at various positions located proximally or distally along the long axis of the leg, thereby allowing adjustment of the position relative to the distal end of the femur and/or the surface of the resected tibia. This may provide an ability to compensate for movement of the femoral resection guide during pinning to ensure a conservative initial resection, or may permit a successive incremental re-resection with the same alignment as the initial resection to provide an incrementally larger prosthetic gap if the initial gap is determined to be too conservative or too tight for implantation of the intended prosthetic device.

In accordance with various embodiments, method 700 need not comprise soft tissue rebalancing prior to establishing the femoral resection guide position or performing the femoral resection. Instead, a balanced and rectangular extension gap may be achieved by establishing the position of the femoral resection guide based on the plane of the resected tibia and/or the position of intramedullary pins left in the tibia following tibial resection. Cuts or releases need not be performed for the medial or lateral collateral ligaments, and these ligaments remain intact throughout the method while a balanced prosthetic gap is produced. Likewise, the mechanical axis of femur relative to the tibia need not be considered in determining the position and alignment of the distal femoral resection, and instead, the distal femoral resection is performed to provide a resected surface that is coplanar with the resected surface of the proximal tibia with balanced tension is applied to the unreleased lateral and medial collateral ligaments. Explained differently, the plane of the femoral resection performed using the methods and devices of the present disclosure may be substantially transverse to the tibial axis in a distracted and extended knee comprising intact collateral ligaments.

The devices and methods disclosed herein provide an extramedullary approach to determining the alignment of and performing a distal femoral resection. The femoral intramedullary canal need not be violated in the course of determining a distal femoral resection position and/or alignment if the devices, kits, and methods of the present disclosure are used. This aspect of the presently disclosed methods provides various significant advantages relative to commonly used methods that rely on placement of an intramedullary rod, including reduced intraoperative patient blood loss and fewer instances of blood transfusions. These advantages, in combination with the reduced trauma to the knee due to the lack of soft tissue releases, produce further benefits of decreased tissue damage, decreased swelling, reduced wound care requirement at the surgical site, decreased joint stiffness, and shortened recovery time. In addition, the devices, kits, and methods described herein reduce the time required to perform a distal femoral resection, and also reduce the complexity of the procedure and the likelihood of occurrence of non-optimal events or creation of iatrogenic instability.

In various embodiments, devices and methods for establishing a proximal tibial resection position to provide a prosthetic gap are provided. A method for establishing a proximal tibial resection position can comprise establishing an axial position and/or alignment of a transverse resection with respect to the distal end of a resected femur. The method described herein can be performed as part of a total knee arthroplasty procedure that may be performed in part using various standard techniques. The proximal tibial resection position and prosthetic gap may be established for the knee in extension with reference to a resected distal femur. Furthermore, while the method described is intended to provide a method for preparing to perform a proximal tibial resection with a desired prosthetic gap, the method may comprise establishing the position of a tibial resection guide without encompassing the step of performing the resection.

Figure 8:
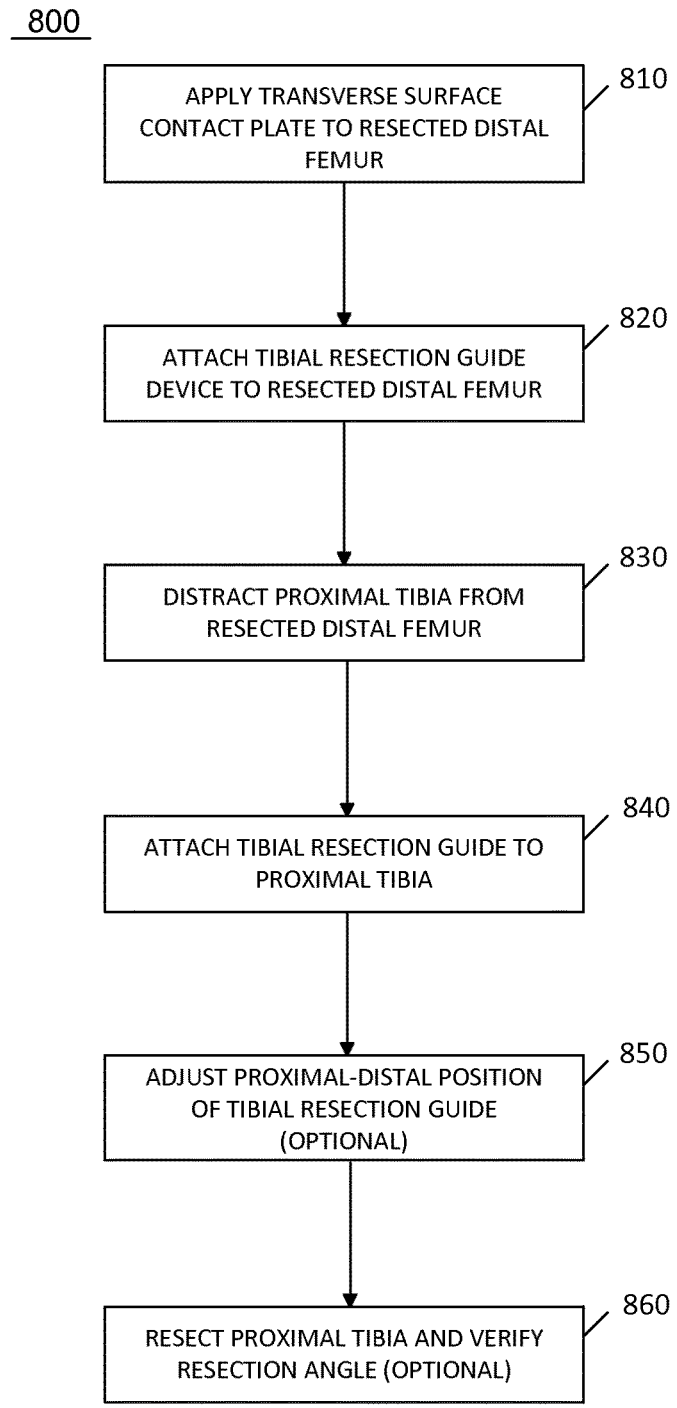
FIG. 8 illustrates a process for establishing a proximal tibial resection position in a total knee arthroplasty procedure according to various embodiments.

With reference now to FIG. 8, a method 800 for establishing a proximal tibial resection position may comprise the steps of: applying a transverse surface contact plate to a resected distal femur 810; attaching a tibial resection guide device to the resected distal femur 820; distracting the proximal tibia from the resected distal femur 830; attaching tibial resection guide to proximal tibia 840; optionally adjusting proximal-distal position of tibial resection guide 850; and optionally resecting the proximal tibia and verifying resection angle 860.

In various embodiments, a method 800 may be performed for establishing a proximal tibial resection position in procedures in which resection of the distal femur is performed using standard techniques prior to resection of the proximal tibia. Various advantages described above relative to the tibia-first method and devices may likewise apply in a femur-first approach, in particular, advantages relative to establishing a balanced prosthetic gap without soft tissue releases. Method 800 may comprise an initial step 810 of applying a transverse surface contact plate 400 to a resected distal femur in a manner similar to that described elsewhere herein relative to application to a resected tibia.

Method 800 may further comprise attaching a tibial resection guide device to the distal femur 820. Step 820 may comprise attaching a device 900 for establishing a proximal tibial resection position, illustrated in FIG. 9 and described in greater detail below, using intramedullary pins that may be left in an anterior aspect of the distal femur following a femoral resection performed using various standard methods. Alternatively, step 820 may comprise attaching an adjustable angle alignment arm 500 to transverse surface contact plate 400 as described above. Alignment arm 500 may further be adjustably coupled to a tibial resection guide 902 portion of device 900, described below.

Figure 9:
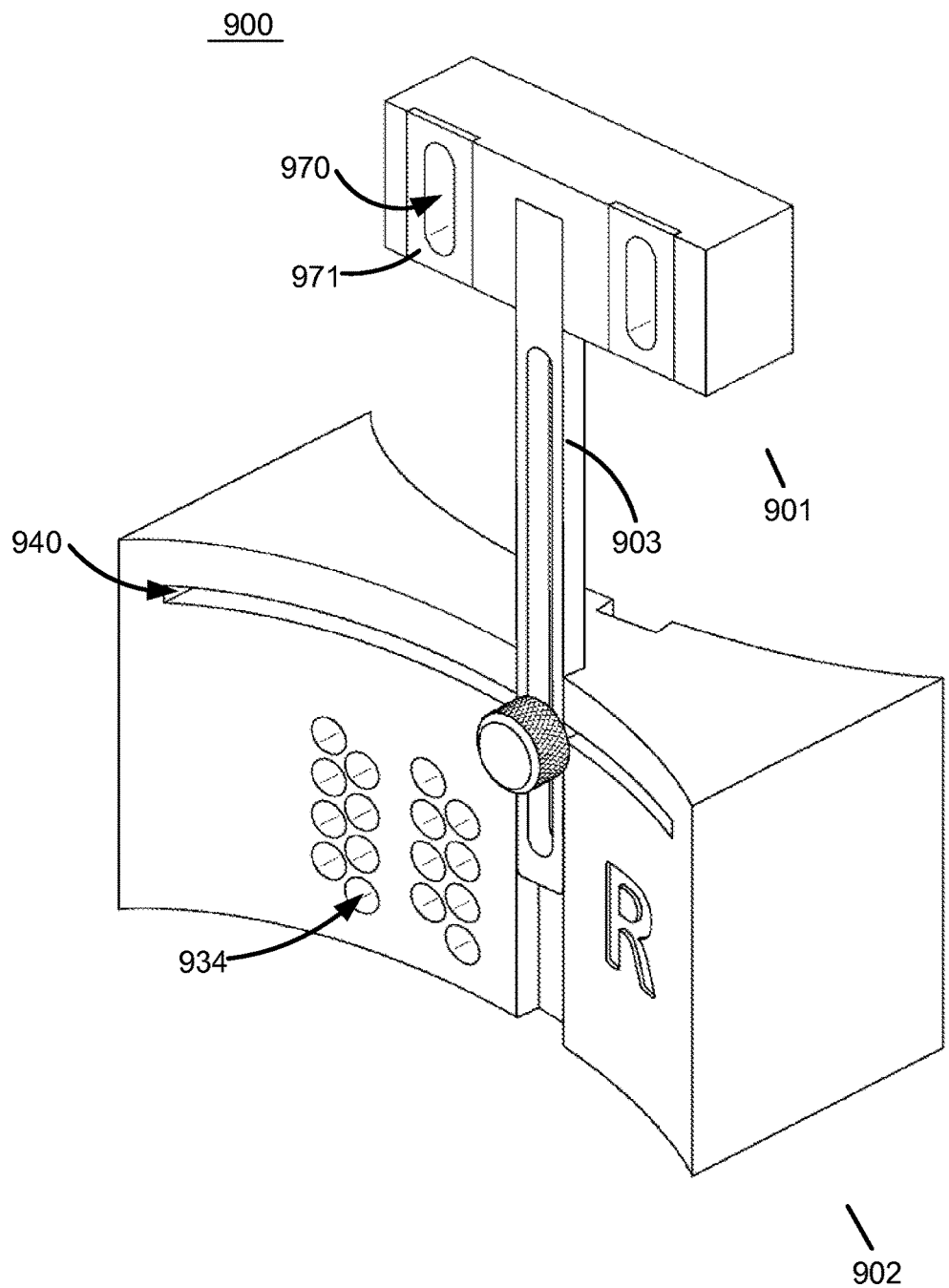
FIG. 9 illustrates a perspective view of a device according to various embodiments.

With reference now to FIG. 9, a device 900 for establishing a proximal tibial resection position in accordance with various embodiments is illustrated. Similar to device 100 for establishing a distal femoral resection position (FIGS. 1A and 1B), device 900 may comprise a femoral support 901 and a tibial resection guide 902. Femoral support 901 may further comprise tibial resection guide alignment arm 903. Tibial resection guide 902 may be removably attached to alignment arm 903 and may comprise an elongated block with concavely curved anterior and posterior surfaces and pairs of pin bores 934 that permit proximal-distal adjustment of resection guide slot 940 relative to the proximal end of a tibia. Tibial resection guide 902 may be reversibly attached to alignment arm 903 for use on either the right or left leg. Alternatively, a tibial pin placement guide (not shown) with a pin bore configuration similar to that of tibial support 101 may be attached to alignment arm 903. A tibial pin placement guide may be used to set pins with a desired anterior-posterior slope (based on the slope of the pin bore in the pin placement guide) for subsequent attachment of resection guide 902 with a corresponding anterior-posterior slope of guide slot 940. In still other embodiments, tibial resection guide 902 may comprise cutouts and removable pin placement inserts comprising pin bores at various anterior-posterior slopes. Following pin placement in the anterior tibia, pin placement inserts may be removed and replaced with inserts comprising pin bores in a pattern that permits proximal-distal adjustment as illustrated for pin bores 934.

Device 900 may comprise various features, materials, and configurations similar to those described above with respect to device 100. In addition, device 900 may comprise pin slots 970 for attachment of femoral support 901 to intramedullary pins placed in the anterior aspect of the distal femur during a femoral resection procedure. The slots 970 may be approximately 10 mm in length and have a proximal-distal orientation that permits femoral support 901 to be tilted in a substantially sagittal plane while substantially limiting lateral motion or rotation in a coronal plane. Slots 970 may be disposed in inserts 971 that may be interchangeably inserted in complementary cutouts in femoral support 901 to accommodate various intramedullary pin widths that may be used in various standard femoral resection procedures.

With reference again to FIG. 8, following attachment of a tibial resection guide, method 800 may further comprise distracting the proximal tibia from the resected distal femur 830. Distraction step 830 may be performed using femoral tibial spreaders 300, with the elongated ring oriented toward the non-resected proximal tibia and the flat rectangular pads oriented toward plate 400. As for distraction step 720 of method 700, distraction step 830 may comprise applying even, balanced tension on the medial and lateral collateral ligaments and further ensuring that the knee is in substantially full extension.

Following distraction step 830, the tibial resection guide may be attached to the proximal tibia in step 840. Step 840 may be performed according to various methods. In various embodiments relying on femoral intramedullary pins to attach device 900 to the distal femur, a pin guide attachment or pin guide inserts may be used to guide insertion of tibial pins at a desired anterior-posterior slope. The surgeon or technician may ensure that device 900 is substantially parallel to the anterior tibial crest during pin placement to achieve the desired anterior-posterior pin slope based on known slope angles of pin guide bores. The configurations of pin slots 970, described above, are suitable to permit rotation of device 900 in a sagittal plane and adjustment of device 900 to a plane approximately parallel to the anterior tibial crest. Alternatively, in various embodiments relying on plate 400 and adjustable angle alignment arm 500, tibial resection guide 902 may be pinned with pins inserted into pin bores 934 having an anterior-posterior slope determined by the angle set at hinge 556 of arm 500. After the tibial resection guide has been attached to the proximal tibia, the alignment arm may be uncoupled from the tibial resection guide and removed.

Following attachment of tibial resection guide and/or placement of tibial pins in step 840, the proximal-distal position of tibial resection guide 902 may optionally be adjusted in step 850 relative to the proximal end of the tibia. The adjustment or position may be made using standard procedures, for example, with the aid of a measurement guide provided by an implant manufacturer. In various embodiments, a proximal-distal adjustment may be made to permit removal of a minimum length of the more worn tibial plateau, for example, approximately 2 mm. The parallel placement of pairs of pin bores 934 to resection guide slot 940 permits proximal-distal adjustment to be made without affecting the established varus-vagus angle or the anterior-posterior slope.

After the proximal-distal position of the tibial resection guide has been established, tibial resection may optionally be performed in step 860. Resection can be performed using resection guide slot 940. Step 860 may further comprise validation of the anterior-posterior slope of the tibial resection using angle validation device 600 (FIG. 6).

As described with reference to method 700 for establishing a femoral resection position, soft tissue rebalancing need not be performed during method 800 for establishing a tibial resection position. A balanced and rectangular extension gap may be achieved with reference to the resected distal femur. Cuts or releases need not be performed for the medial or lateral collateral ligaments, and these ligaments remain intact throughout the method while a balanced prosthetic gap is produced.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. Reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. All structural and functional equivalents to the elements of the above-described embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. A device for establishing a distal femoral resection position in a total knee arthroplasty procedure comprising:
    a tibial support comprising a tibial support cutout and a tibial support insert comprising a pin bore, wherein the tibial support insert is disposed in the tibial support cutout;
    a femoral resection guide alignment arm at least one of coupled to or integral with the tibial support and extending from the tibial support;
    a femoral resection guide comprising a guide body having an anterior face, wherein the alignment arm is disposed along the anterior face of the guide body, wherein the femoral resection guide is configured to be removably attached to a distal femur adjacent to a posterior face of the guide body opposite the anterior face; and
    an alignment arm coupling component coupled to the femoral resection guide, wherein the alignment arm coupling component provides a mechanical force on the alignment arm such that the alignment arm is detachably coupled to the femoral section guide,
wherein the alignment arm is adjustably coupled to the femoral resection guide, providing a range of relative coupling positions of the femoral resection guide relative to the tibial support.

2. The device of claim 1, wherein the alignment arm is detachable from the femoral resection guide while the femoral resection guide is removably attached to the distal femur.

3. The device of claim 1, wherein the tibial support comprises a plurality of pin bores disposed between an anterior face and a posterior face of the tibial support, and wherein the plurality of pin bores is configured to engage a plurality of pins inserted in an anterior aspect of a proximal tibia.

4. The device of claim 1, wherein the tibial support insert comprises a plurality of pin bores.

5. The device of claim 1, wherein the tibial support comprises a plurality of tibial support cutouts.

6. The device of claim 1, wherein the femoral resection guide comprises a resection guide slot.

7. The device of claim 6, wherein the femoral resection guide slot spans greater than 90% of a length of the femoral resection guide.

8. The device of claim 6, wherein the femoral resection guide slot comprises a femoral resection guide slot angle that is substantially parallel to a femoral resection guide pin bore disposed through the guide body from the anterior face to a posterior face of the guide body.

9. The device of claim 1, wherein the guide body comprises an alignment arm receiving channel recessed into and along the anterior face defined by parallel side walls and a channel bottom, wherein the alignment arm is disposed in the alignment arm receiving channel.

10. The device of claim 1, wherein the guide body comprises a threaded bore, and the alignment arm coupling component comprises a threaded shaft complementary to the threaded bore, wherein the femoral resection guide is coupled to the alignment arm coupling component by the threaded shaft of the alignment arm coupling component being disposed in the threaded bore of the guide body.

11. The device of claim 10, wherein the alignment arm comprises an alignment arm slot, through which the threaded shaft of the alignment arm coupling component is disposed, such that the alignment arm is between a knurled knob of the alignment arm coupling component and the guide body.

12. A device for establishing a distal femoral resection position in a total knee arthroplasty comprising:
    a tibial support and a tibial support cutout in the tibial support;
    a femoral resection guide alignment arm at least one of coupled to or integral with the tibial support and extending from the tibial support;
    a tibial support insert comprising a plurality of pin bores, wherein the tibial support insert is disposed within the tibial support cutout;
    a femoral resection guide comprising a guide body having an anterior face and an alignment arm receiving channel recessed into and along the anterior face, a resection guide slot, and a plurality of pin bores, wherein the alignment arm is disposed within the alignment arm receiving channel; and
    an alignment arm coupling component coupled to the femoral resection guide, wherein the alignment arm coupling component provides a mechanical force on the alignment arm such that the alignment arm is detachably coupled to the femoral section guide, wherein the alignment arm is adjustably coupled to the femoral resection guide.

13. The device of claim 12, wherein the guide body comprises a threaded bore disposed in the alignment arm receiving channel, and the alignment arm coupling component comprises a threaded shaft complementary to the threaded bore, wherein the femoral resection guide is coupled to the alignment arm coupling component by the threaded shaft of the alignment arm coupling component being disposed in the threaded bore of the guide body.

14. The device of claim 13, wherein the alignment arm comprises an alignment arm slot, through which the threaded shaft of the alignment arm coupling component is disposed, such that the alignment arm is between a knurled knob of the alignment arm coupling component and the guide body.

* * * * *